United States Patent [19]

Mita et al.

[11] Patent Number: 5,350,860
[45] Date of Patent: Sep. 27, 1994

[54] BICYCLIC COMPOUNDS

[75] Inventors: Shiro Mita, Ashiya; Yoichi Kawashima, Kyoto; Ken-ichi Fujimura, Osaka; Hiroshi Suhara, Osaka; Masahiro Okamoto, Uji, all of Japan

[73] Assignee: Santen Pharmaceutical Co., Ltd., Osaka, Japan

[21] Appl. No.: 5,611

[22] Filed: Jan. 19, 1993

[30] Foreign Application Priority Data

Jan. 31, 1992 [JP] Japan .................... 4-060887

[51] Int. Cl.$^5$ ............... C07D 497/04; C07G 495/04
[52] U.S. Cl. ....................... 548/453; 549/9
[58] Field of Search ............. 548/453; 549/9; 514/412, 431

[56] References Cited

FOREIGN PATENT DOCUMENTS

WO92/12129 7/1992 World Int. Prop. O. .

OTHER PUBLICATIONS

Bach et al., Thymulin, A Zinc–Dependent Hormone, Med. Oncol. & Tumor Pharmacother. vol. 6, No. 1, pp. 25–29, 1989, Great Britain.

*Primary Examiner*—David B. Springer
*Attorney, Agent, or Firm*—Frishauf, Holtz, Goodman & Woodward

[57] ABSTRACT

A compound of the formula [I].

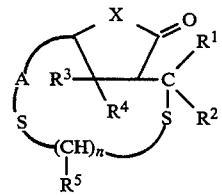

The compounds of this invention has excellent thymulin-line activities and expected to be useful for treatment of various diseases such as immunodeficiency and autoimmune diseases.

15 Claims, No Drawings

BICYCLIC COMPOUNDS

FIELD OF THE INVENTION

This invention relates to the novel bicyclic compounds which are useful for treatment of various diseases caused by immune disorders such as immunodeficiency and autoimmune diseases.

BACKGROUND OF THE INVENTION

There are many active studies on mechanisms and therapeutic agents for various diseases due to immune disorders or immune depression caused by carcinostatic drugs. It is known that thymulin, a nonapeptide produced in the thymus, forms a complex with zinc and improves a depressed immunity (Med. Oncol. & Tumor Pharmacother. 6, 25-29, 1989).

However, there remain many problems in practical user, of thymulin. For example, the availability of thymulin is limited due to a small yield in the thymus and duration of the activity thereof is short because thymulin is easily decomposed by endogenous enzymes.

Therefore, synthetic compounds are desired which have a long lasting activity and can be prepared in a large amount. As such synthetic compounds, lactone or lactam compounds having two intermolecular sulfur atoms in the side chain are proposed (PCT/JP92/00002). As shown in the PCT application, the lactone or lactam compounds show excellent thymulin-like activities.

However, it is further desired to study the derivatives thereof to find another useful compounds.

The inventors intended to convert the lactone or lactam compounds disclosed in PCT/JP92/00002 into bicyclic compounds and succeeded in obtaining novel bicyclic compounds which have excellent thymulin-like activities.

DETAILED DESCRIPTION OF THE INVENTION

This invention relates to a compound of the formula [I] and pharmaceutically acceptable salts thereof,

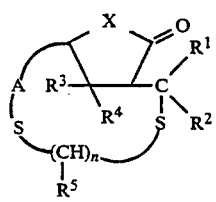

[I]

wherein
$R^1$ and $R^2$ are the same or different and each is hydrogen or lower alkyl;
$R^3$ and $R^4$ are the same or different and each is hydrogen, lower alkyl, carboxy or lower alkoxycarbonyl;
$R^5$ is hydrogen or lower alkyl;
X is oxygen or $NR^6$;
$R^6$ is hydrogen, lower alkyl, lower alkoxy, phenyl lower alkyl or phenyl lower alkoxy, and the said lower alkyl can be substituted by carboxy, lower alkoxycarbonyl, amino, lower alkylamino, lower alkoxycarbonylamino or phenyl lower alkylamino, and the phenyl ring of the said phenyl lower alkyl, phenyl lower alkoxy or phenyl lower alkylamino can be substituted by lower alkyl, lower alkoxy, halogen, carboxy or lower alkoxycarbonyl;
A is straight or branched lower alkylene;
n is 0 or 1,
the same shall be applied hereinafter.

The terms defined above are explained as follows in more detail.

The term "lower alkyl" intends to designate straight or branched lower alkyl having 1 to 6 carbon atoms exemplified by methyl, ethyl, propyl, hexyl, iso-propyl and t-butyl. The term "lower alkoxy" intends to designate straight or branched lower alkoxy having 1 to 6 carbon atoms exemplified by methoxy, ethoxy, propoxy, hexyloxy, iso-propoxy and t-butoxy. The term "lower alkylene" intends to designate straight or branched lower alkylene having 1 to 6 carbon atoms exemplified by methylene, ethylene, trimethylene, tetramethylene, hexamethylene, (dimethyl)methylene and (diethyl)methylene. The term "halogen" intends to designate fluorine, chlorine, bromine and iodine.

Examples of the pharmaceutically acceptable salts are sodium salt, potassium salt, calcium salt, magnesium salt, zinc salt, hydrochloric acid salt, sulfuric acid salt, phosphoric acid salt, lactic acid salt, maleic acid salt, fumaric acid salt and oxalic acid salt.

The compounds of this invention can be prepared from the compounds disclosed in PCT/JP92/00002.

Typical synthetic methods of the compounds of the formula [I] are shown in the following a) and b).

a) A cyclization method by oxidizing a dithiol compound of the formula [II].

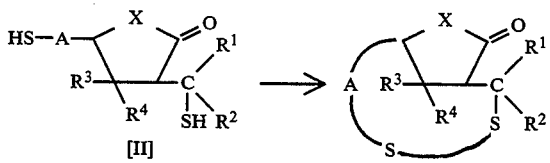

b) A cyclization method by reacting a dithiol compound of the formula [II] with a compound of the formula [III] in a presence of boron trifluoride diethyl ether complex.

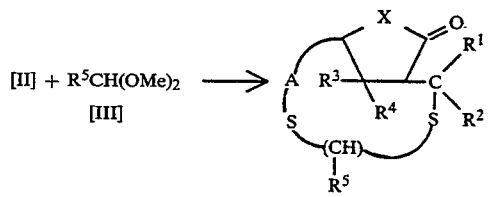

In the above a) and b) methods, when X represents $NR^6$ in which $R^6$ is used as a protecting group of NH group, the protecting group can be removed in a desirable step by a usual method. Further, when $R^6$ contains protected amino group, such protection can be released by a usual method.

When the obtained bicyclic compound contains ester group, such ester can be hydrolyzed to carboxylic acid by a usual method.

The compounds prepared by the above methods can be converted into the salts as mentioned before by a usual method.

The compounds of the formula [I] have optical isomers or stereoisomers, and these isomers are included in this invention.

The inventors examined pharmacological effects of the compounds of this invention and found that the compounds had excellent thymulin-like activities. The compounds of this invention are expected to be useful for treatment of various diseases such as immunodeficiency and autoimmune diseases, caused by immune disorders as expected in thymulin. There are various diseases caused by immune disorders, for example, rheumatoid arthritis, chronic hepatitis, anemia, systemic lupus erythematosus, primary immunodeficiency or agamma-globulinemia. The compounds of this invention are expected to be useful for treatment of such diseases.

The compounds of this invention can be administered orally or parenterally. As the dosage forms, tablet, capsule, soft capsule, injection, etc., can be used. The preparations can be produced by a usual method. For example, oral preparations such as tablet, capsule, soft capsule and granule can be produced by adding diluent such as lactose, starch, crystalline cellulose or vegetable oil; lubricant such as magnesium stearate or talc; binder such as hydroxypropyl cellulose or polyvinylpyrrolidone; disintegrator such as carboxymethylcellulose calcium; coating agent such as hydroxypropylmethylcellulose, macrogol or silicone resin; coating film such as gelatin, if necessary. The dosage of the compounds of this invention can be adjusted depending on symptom, dosage form, etc. The usual daily dosage is 1–1000 mg, preferably 1–200 mg, which can be given in one or a few divided doses.

EXAMPLE

Example 1

(6,6-dimethyl-9-oxo)-3,5-dithia-8-oxabicyclo[5, 2, 1]decane

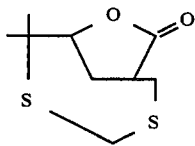

To a stirred solution of boron trifluoride diethyl ether complex (0.12 ml) and acetic acid (0.25 ml) in chloroform (3 ml), cis-4-(1-mercapto-1-methylethyl)-2-mercaptomethyl-4-butanolide (200 mg) and methylal (83 mg) dissolved in chloroform (1 ml) was added dropwise, while refluxing under nitrogen atmosphere. The mixture was refluxed for further three hours. After cooling, the mixture was poured into saturated aqueous sodium hydrogencarbonate solution and extracted with methylene chloride. The organic layer was washed with saturated aqueous sodium hydrogencarbonate solution and saturated sodium chloride solution. The organic layer was dried over anhydrous sodium sulfate and concentrated in vacuo. The oily residue was purified by a silica gel column chromatography to give 21 mg of the titled compound.

IR(KBr, cm$^{-1}$): 2966, 2922, 1763, 1468, 1362, 1275, 1208, 1171, 1048, 1011, 857, 775, 724

Following compounds can be prepared by the similar method as Example 1.

(9-oxo )-3,5-dithia-8-oxabicyclo [5,2,1 ]decane (2-methyl-9-oxo)-3,5-dithia-8-oxabicyclo [5, 2,1]decane ( 10-methyl-9-oxo )-3,5-dithia-8-oxabicyclo[5,2,1 ]decane ( 10-oxo )- 3,5-dithia-9-oxabicyclo[6,2,1 ]undecane

Example 2

(6, 6-dimethyl-9-oxo)-3,5-dithia-8-azabicyclo[5,2,1]-decane

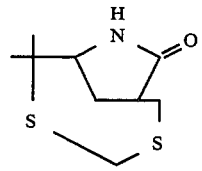

To a stirred solution of boron trifluoride diethyl ether complex (60µl) and acetic acid (126µl) in chloroform (2 ml), cis-4-(1-mercapto-1-methylethyl)-2-mercaptomethyl-4-butanelactam (100 mg) and methylal (41 mg) dissolved in chloroform (1 ml) was added dropwise, while refluxing under nitrogen atmosphere. The mixture was refluxed for further three hours. After cooling, the mixture was poured into saturated aqueous sodium hydrogencarbonate solution and extracted with methylene chloride. The organic layer was washed with saturated aqueous sodium hydrogencarbonate solution and saturated sodium chloride solution. The organic layer was dried over anhydrous sodium sulfate and concentrated in vacuo. The oily residue was purified by a silica gel column chromatography to give 11 mg of the titled compound.

mp 162.6°–167.3 ° C.

IR(KBr, cm$^{-1}$): 3185, 3076, 2919, 1680, 1440, 1380, 1276, 703

Following compounds can be prepared by the similar method as Example 2.

(8-benzyl-9-oxo)-3,5-dithia-8-azabicyclo [5,2,1]decane

[8-(4-carboxyphenylmethyl)-6,6-dimethyl-9-oxo]-3,5-dithia-8-azabicyclo [5,2,1]decane (8-carboxymethyl- 6,6-dimethyl- 9-oxo)-3,5-dithia-8-azabicyclo[5,2,1 ]decane (2-methyl-9-oxo)-3,5-dithia-8-azabicyclo[5,2,1]decane (10-methyl-9-oxo)-3,5-dithia-8-azabicyclo[5,2,1]decane (8-isopropyl-9-oxo)-3,5-dithia-8-azabicyclo[5,2,1 ]decane

[6,6-dimethyl-8-(5-tert-butoxycarbonylaminopentyl)-9-oxo ]-3,5-dithia-8-azabicyclo [5,2,1]decane

[6,6-dimethyl-8-(5-aminopentyl)-9-oxo]-3,5-dithia-8-azabicyclo [5,2,1 ]decane (6,6-dimethyl-10-oxo)-3,5-dithia-9-azabicyclo[6, 2,1 ]undecane

Example 3

(5, 5-dimethyl-8-oxo)-3, 4-dithia-7-oxabicyclo[4, 2,1 ]nonane

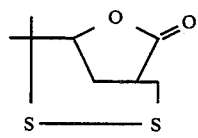

To a stirred solution of triethylamine (85µl) in ethyl acetate (5 ml), cis-4-(1-mercapto-1-methylethyl)-2-mercaptomethyl-4-butanolide (57 mg) dissolved in ethyl acetate (5 ml) and iodine (74 mg) dissolved in ethyl acetate (5 ml) were added dropwise simultaneously, and the mixture was stirred for 30 minutes at room temperature. The mixture was washed with aqueous sodium thiosulfate solution and saturated sodium chloride solution. The organic layer was dried over anhydrous sodium sulfate and concentrated in vacuo to give 54 mg of the titled compound.

mp 95.7°–99.3° C.

IR(KBr, cm$^{-1}$): 2960, 1772, 1452, 1347, 1242, 1133

Following compounds can be prepared by the similar method as Example 3.

(8-oxo)-3,4-dithia-7-oxabicyclo[4,2,1]nonane (2-methyl-8-oxo)-3,4-dithia-7-oxabicyclo[4,2,1]nonane (9-methyl-8-oxo)-3,4-dithia-7-oxabicyclo[4,2,1]nonane (9-oxo)-3,4-dithia-8-oxabicyclo[5,2,1]decane Example 4

(5,5-dimethyl-8-oxo)-3,4-dithia-7-azabicyclo[4,2,1]nonane

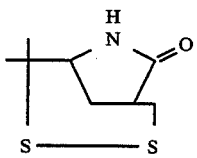

To a stirred solution of triethylamine (74 μl) in ethyl acetate (5 ml), cis-4-(1-mercapto-1-methylethyl)-2-mercaptomethyl-4-butanelactam (50 mg) dissolved in ethyl acetate (5 ml) and iodine (64 mg) dissolved in ethyl acetate (5 ml) were added dropwise simultaneously, and the mixture was stirred for 30 minutes at room temperature. The mixture was washed with aqueous sodium thiosulfate solution and saturated sodium chloride solution. The organic layer was dried over anhydrous sodium sulfate and concentrated in vacuo to give 43 mg of the titled compound.

mp 181.7°–182.4° C. (benzene - cyclohexane)

IR(KBr, cm$^{-1}$): 3180, 3076 2894 1693, 1454 1384, 1285, 826

Following compounds can be prepared by the similar method as Example 4.

(7-benzyl-8-oxo)-3,4-dithia-7-azabicyclo[4,2,1]nonane

[7 -(4 -carboxyphenylmethyl)-5,5-dimethyl-8-oxo ]-3,4 -dithia- 7-azabicyclo [4,2,1 ]nonane (7-carboxymethyl-5,5-dimethyl-8-oxo)-3,4-dithia-7-azabicyclo[4,2,1]nonane (2-methyl-8-oxo)-3,4-dithia-7-azabicyclo[4,2,1]nonane (9-methyl-8-oxo)-3,4-dithia-7-azabicyclo[4,2,1]nonane (7-isopropyl-8-oxo)-3,4-dithia-7-azabicyclo[4,2,1]nonane

[5,5-dimethyl-7 -(5-tert-butoxycarbonylaminopentyl)-8-oxo ]-3,4-dithia-7-azabicyclo [4,2,1]nonane

[5,5-dimethyl-7-(5-aminopentyl)-8-oxo]-3,4-dithia-7-azabicyclo [4,2,1]nonane (5,5-dimethyl-9-oxo)-3,4-dithia-8-azabicyclo[5,2,1]decane

PHARMACOLOGICAL TEST

Thymulin-like activities of the compounds of this invention were examined by modifying the method reported by J. F. Bach et al. (Bull. Inst. Pasteur, 76, 325 (1978)).

Experimental Method

A thymus of C57BL/6 strain male mouse (10 weeks age, 4 mice a group) was removed. After about two weeks, a spleen of the mouse was extracted and a spleen cells suspension (1–10$^8$ cells/ml in Hank's solution) was prepared. To 100 μl of the cells suspension, 100 μl of Hank's solution dissolving a test compound and zinc chloride in 1:1 molar ratio was added. After a 30 minutes incubation at 37° C., 50 μl of azathiopurine (50 μg/ml in Hank's solution) was added and the mixture was incubated further 60 minutes at the same temperature. To the mixture, 50 μl of sheep red blood cells (1×10$^8$ cells/ml in Hank's solution) was added and mixed. The mixture was incubated at 4° C. for one night. After gently shaking, E-rosette forming cells (E-RFC) were measured. As an active control, a solution of thymulin and zinc chloride, which were dissolved in Hank's solution in a concentration of 1×10$^{-14}$M and 1:1 molar ratio, was used and it was treated by the same manner as the case of the test compound.

Result

Thymulin-like activity was calculated by the following formula.

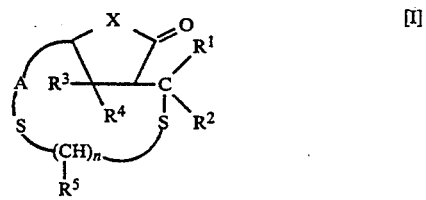

The activities were measured on typical compounds of this invention, which showed over than 50% of thymulin-like activity at a dose of lower than 10$^{-7}$M.

What we claim is:

1. A compound of the formula [I] and pharmaceutically acceptable salts thereof,

[I]

wherein

R$^1$ and R$^2$ are the same or different and each is hydrogen or a straight or branched chain alkyl having 1 to 6 carbon atoms;

R$^3$ and R$^4$ are the same or different and each is hydrogen, a straight or branched chain alkyl having 1 to 6 carbon atoms, carboxy or lower alkoxycarbonyl;

R$^5$ is hydrogen or straight or branched chain alkyl having 1 to 6 carbon atoms;

X is oxygen or NR$^6$;

R$^6$ is hydrogen, lower alkyl, lower alkoxy, phenyl lower alkyl or phenyl lower alkoxy, and the said lower alkyl can be substituted by carboxy, lower alkoxycarbonyl, amino, lower alkylamino, lower alkoxycarbonylamino or phenyl lower alkylamino, and the phenyl ring of the said phenyl lower alkyl, phenyl lower alkoxy or phenyl lower alkylamino can be substituted by lower alkyl, lower alkoxy, fluorine, chlorine, bromine, iodine, carboxy or lower alkoxycarbonyl wherein each lower alkyl is a straight or branched alkyl having 1 to 6 carbon atoms, and each lower alkoxy is a straight or branched alkoxy having 1 to 6 carbon atoms;

A is straight or branched alkylene having 1 to 6 carbon atoms, n is 0 to 1.

2. The compound as in claim 1 wherein X is oxygen, $R^5$ is hydrogen and n is 1.

3. The compound as in claim 1 wherein X is oxygen and n is 0.

4. The compound as in claim 1 wherein X is $NR^6$, $R^5$ is hydrogen and n is 1.

5. The compound as in claim 1 wherein X is $NR^6$ and n is 0.

6. (6,6-dimethyl-9-oxo)-3,5-dithia-8-oxabicyclo[5,2,1]decane.

7. (6,6-dimethyl-9-oxo)-3,5-dithia-8-azabicyclo[5,2,1]decane.

8. (5,5-dimethyl-8-oxo)-3,4-dithia-7-oxabicyclo[4,2,1]nonane.

9. (5,5-dimethyl-8-oxo)-3,4-dithia-7-azabicyclo[4,2,1]nonane.

10. A pharmaceutical composition comprising a compound of the formula [I] or pharmaceutically acceptable salts thereof and a pharmaceutically acceptable ingredient.

11. The compound of claim 1 selected from the group consisting of
(9-oxo)-3,5-dithia-8-oxabicyclo]5,2,1]decane,
(2-methyl-9-oxo)-3,5-dithia-8-oxabicyclo[5,2,1]decane,
(10-methyl-9-oxo)-3,5-dithia-8-oxabicyclo[5,2,1]decane and
(10-oxo)-3,5-dithia-9-oxabicyclo[6,2,1]undecane.

12. The compound of claim 1 selected from the group consisting of
(8-benzyl-9-oxo)-3,5-dithia-8-azabicyclo[5,2,1]decane,
[8-(4-carboxyphenylmethyl)-6,6-dimethyl-9-oxo]-3,5-dithia-8-azabicyclo [5,2,1]decane,
(8-carboxymethyl-6,6-dimethyl-9-oxo)-3,5-dithia-8-azabicyclo[5,2,1]decane,
(2-methyl-9-oxo)-3,5-dithia-8-azabicyclo[5,2,1]decane,
(10-methyl-9-oxo)-3,5-dithia-8-azabicyclo[5,2,1]decane,
(8-isopropyl-9-oxo)-3,5-dithia-8-azabicyclo[5,2,1]decane,
[6,6-dimethyl-8-(5-tert-butoxycarbonylaminopentyl)-9-oxo]-3,5-dithia-8-azabicyclo [5,2,1]decane,
[6,6-dimethyl-8-(5-aminopentyl)-9-oxo]-3,5-dithia-8-azabicyclo [5,2,1]decane and
(6,6-dimethyl-10-oxo)-3,5-dithia-9-azabicyclo[6,2,1]undecane.

13. The compound of claim 1 selected from the group consisting of
(8-oxo)-3,4-dithia-7-oxabicyclo[4,2,1]nonane,
(2-methyl-8-oxo)-3,4-dithia-7-oxabicyclo[4,2,1]nonane,
(9-methyl-8-oxo)-3,4-dithia-7-oxabicyclo[4,2,1]nonane and
(9-oxo)-3,4-dithia-8-oxabicyclo[5,2,1]decane.

14. The compound of claim 1 selected from the group consisting of
(7-benzyl-8-oxo)-3,4-dithia-7-azabicyclo[4,2,1]nonane,
[7-(4-carboxyphenylmetnyl)-5,5-dimethyl-8-oxo]-3,4-dithia-7-azabicyclo [4,2,1]nonane,
(7-carboxymethyl-5,5-dimethyl-8-oxo)-3,4-dithia-7-azabicyclo[4,2,1]nonane,
(2-methyl-8-oxo)-3,4-dithia-7-azabicyclo[4,2,1]nonane,
(9-methyl-8-oxo)-3,4-dithia-7-azabicyclo[4,2,1]nonane,
(7-isopropyl-8-oxo)-3,4-dithia-7-azabicyclo[4,2,1]nonane,
[5,5-dimethyl-7-(5-tert-butoxycarbonylaminopentyl)-8-oxo]-3,4-dithia-7-azabicyclo [4,2,1]nonane,
[5,5-dimethyl-7-(5-aminopentyl)-8-oxo]-3,4-dithia-7-azabicyclo [4,2,1]nonane and
(5,5-dimethyl-9-oxo)-3,4-dithia-8-azabicyclo[5,2,1]decane.

15. The pharmaceutical composition of claim 10 wherein said compound of formula [I] is
(6,6-dimethyl-9-oxo)-3,5-dithia-8-oxabicyclo[5,2,1]decane,
(6,6-dimethyl-9-oxo)-3,5-dithia-8-azabicyclo[5,2,1]decane,
(5,5-dimethyl-8-oxo)-3,4-dithia-7-oxabicyclo[4,2,1]nonane or
(5,5-dimethyl-8-oxo)-3,4-dithia-7-azabicyclo[4,2,1]nonane.

* * * * *